United States Patent [19]

Inomata et al.

[11] Patent Number: 5,288,890

[45] Date of Patent: Feb. 22, 1994

[54] FLUORINE-CONTAINING ORGANOSILICON COMPOUND AND PROCESS OF PRODUCING THE SAME

[75] Inventors: Hiroshi Inomata, Annaka; Yasuo Tarumi, Takasaki; Hiromasa Yamaguchi, Annaka; Kenichi Fukuda, Takasaki; Kazutoshi Munezawa, Annaka, all of Japan

[73] Assignee: Shin-Etsu Chemical Co., Ltd., Tokyo, Japan

[21] Appl. No.: 24,371

[22] Filed: Mar. 1, 1993

[30] Foreign Application Priority Data

Feb. 28, 1992 [JP] Japan .................. 4-078499

[51] Int. Cl.$^5$ .................. C07F 7/08
[52] U.S. Cl. .................. 556/440
[58] Field of Search .................. 556/440

[56] References Cited

U.S. PATENT DOCUMENTS

| | | | |
|---|---|---|---|
| 3,012,006 | 12/1961 | Holbrook et al. | 556/440 X |
| 3,317,369 | 5/1967 | Clark et al. | |
| 3,394,162 | 7/1968 | Braun | 556/440 |
| 3,560,542 | 2/1971 | Kim et al. | |
| 3,746,734 | 7/1973 | Berger et al. | |
| 3,798,251 | 3/1974 | Meiller et al. | 556/440 |
| 3,833,632 | 9/1974 | Meiller et al. | 556/440 |
| 4,965,387 | 10/1990 | Shinohara et al. | 556/440 |
| 5,070,215 | 12/1991 | Bambury et al. | 55/440 X |

FOREIGN PATENT DOCUMENTS 476762  8/1969  Switzerland .

*Primary Examiner*—Paul F. Shaver
*Attorney, Agent, or Firm*—Oblon, Spivak, McClelland, Maier & Neustadt

[57] ABSTRACT

A fluorine-containing organosilicon compound having the formula (1):

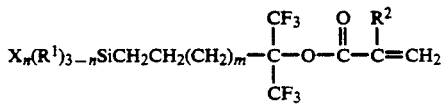

wherein X is a hydrolizable group, $R^1$ is a monovalent organic group, $R^2$ is a methyl group or a hydrogen atom, n is an integer of 1, 2 or 3, and m is an integer of 0 or 1, and a process of producing said compound. The compound may be used as a silane coupling agent capable of improving not only the strength of laminated sheets of polyester resin and glass and polyester resin concrete but also water and heat resistances.

5 Claims, No Drawings

FLUORINE-CONTAINING ORGANOSILICON COMPOUND AND PROCESS OF PRODUCING THE SAME

BACKGROUND OF THE INVENTION

1. Field of the Invention

The present invention relates to a fluorine-containing organosilicon compound containing in the molecule a hydrolizable group bonded to a silicon and an acryloxyl or methacryloxyl group.

2. Description of the Prior Art

An organosilicon compound having the formula (4):

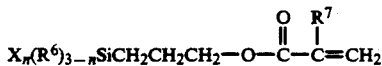

wherein X is a hydrolizable group, $R^6$ is a monovalent organic group, $R^7$ is a methyl group or a hydrogen atom and n is an integer of 1, 2 or 3, for example, has a silicon-bonded hydrolizable group X-Si group that can react with glass, metal or silica and an acryloxyl or methacryloxyl group that can react with organic materials such as synthetic resins, and is known to be used in the prior art as a silane coupling agent for laminated sheets of polyester resin and glass for its high performance in improving the mechanical strength and electric properties. The compound is also known to be highly effective in improving the strength when added to polyester resin concrete.

However, water resistance and heat resistance obtained by the prior art organosilicon compound were insufficient.

SUMMARY OF THE INVENTION

The present invention therefore aims at providing a novel organosilicon compound which, when added to synthetic resins or organic materials as a silane coupling agent, improves not only mechanical strength and electric properties but both water and heat resistances as well.

In order to achieve the object of the invention, the present invention provides a fluorine-containing organosilicon compound having the formula (1):

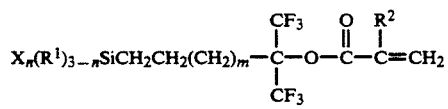

wherein X is a hydrolizable group, $R^1$ is a monovalent organic group, $R^2$ is a methyl group or a hydrogen atom, n is an integer of 1, 2 or 3, and m an integer of 0 or 1.

The present invention also provides a process of producing a fluorine-containing organosilicon compound having the formula (1) above which comprises effecting addition-reaction of a fluorine-containing organic compound having the formula (2):

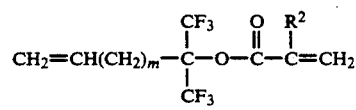

wherein $R^2$ is a methyl group or a hydrogen atom, and m is an integer of 0 or 1, with a silane compound having the general formula (3):

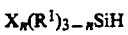

wherein X is a hydrolizable group, $R^1$ is a monovalent organic group, n is an integer of 1, 2 or 3, in the presence of a transition metal or its compound.

The fluorine-containing organosilicon compound according to the present invention is a novel compound that can be used as a coupling agent for laminated sheets of polyester resin and glass and to improve the strength of polyester resin concrete. It is expected to contribute to improving not only the mechanical strength and electric properties but also water and heat resistances.

DETAILED DESCRIPTION OF PREFERRED EMBODIMENTS

Fluorine-containing Organosilicon Compound

The fluorine-containing organosilicon compound of the present invention contains a fluorine-containing group $—C(CF_3)_2—$ and is represented by the formula (1) above.

Examples of the hydrolizable group X in the formula (1) include a halogen atom of fluorine, chlorine, bromine or iodine, an alkoxy group represented by $—OR^3$ and an amino group expressed by $—NR^4R^5$, wherein $R^3$ is a monovalent organic group such as an alkyl group having 1 to 10 carbon atoms such as methyl, ethyl, n-propyl, isopropyl and n-butyl groups, a fluoroalkyl group having 2 to 15 carbon atoms such as trifluoroethyl group, an acetyl group, an acyl group such as propyonyl group, and an alkenyl group having 2 to 5 carbon atoms such as isopropenyl group. $R^4$ and $R^5$ are each a monovalent organic group which may be the same or different; for example an alkyl group having 1 to 10 carbon atoms such as methyl group, ethyl group or isopropyl group.

Examples of monovalent organic compound $R^1$ in the formula (1) specifically include an alkyl group having 1 to 10 carbon atoms such as methyl group, ethyl group and n-propyl group, an aryl group having 6 to 10 carbon atoms such as phenyl group and toluyl group, and a fluoroalkyl group having 3 to 15 carbon atoms such as trifluoropropyl group.

Production Process

The fluorine-containing organosilicon compound of the present invention can be obtained by the process which comprises effecting addition-reaction of said fluorine-containing organic compound having the formula (2) above with a silane compound having the formula (3) above in the presence of a catalyst.

The compound having the general formula (2) can be produced by, for example, reacting an alcohol having the formula (5):

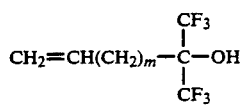

wherein m is as defined above, with an acrylic acid or methacrylic acid in the presence of a dehydrating agent such as fuming sulfuric acid. It can also be obtained by reacting the alcohol represented by the formula (5)

above with an alkyl lithium to produce a lithium alkoxide, which in turn is reacted with an acrylic chloride or methacrylic chloride.

Examples of a catalyst used in the addition-reaction of the fluorine-containing organic compound of the formula (2) with the silane compound of the formula (3) include transition metals and their compounds such as a salt or complex, and more particularly, metals such as Pt, Rh and Pd. Examples of salts or complexes of the transition metals include an olefin modified complex of $H_2PtCl_6$, alcohol modified complex of $H_2PtCl_6$, vinylsiloxane modified complex of $H_2PtCl_6$, $RhCl_3$, $Rh(CH_3COCHCOCH_3)_3$, $Rh(PPh_3)_3Cl$, $Rh(PPh_3)_3Br$, $Rh_2(AcO)_4$, $Rh(PPh_3)_2(CO)Cl$, $Rh(\eta^4-C_7H_8)Cl$, $Rh(CH_3COCHCOCH_3)(CO)_2$, $Rh_4(CO)_{12}$, $Rh(CO)_{16}$, $Rh(PPh_3)_3(CO)H$, $(NH_4)_2PdCl_6$, $(NH_4)_2PdCl_4$, $Pd(CH_3COCHCOCH_3)_2$, $Pd(PhCN)_2Cl_2$, $Pd(PPh_3)_2Cl_2$, and $Pd(PPh_3)_4$ wherein Ph is the phenyl group and Ac represents the acetyl group.

For the synthesis of the fluorine-containing organosilicon compound according to the present invention, a silane compound having the formula (3) and a catalyst for addition-reaction are charged in a reaction vessel, and added dropwise with a fluorine-containing organic compound having the general formula (2) while maintaining the mixture at a prescribed temperature to give rise to addition-reaction. The reaction temperature is normally between 30° and 150° C., and more preferably between 60° and 130° C. Progress of the reaction can be monitored by measuring the amount of the starting materials consumed and the amount of the reaction product formed using chromatographic analysis method. Normally, the addition-reaction is completed in about 30 minutes to 48 hours. If the consumption of the starting materials stops before the completion of the addition-reaction, the reaction can be resumed by adding the catalyst. Upon completion, the reaction mixture can be distilled to isolate and purify the fluorine-containing organosilicon compound. There are no particular restrictions regarding the order of charging said silane compound, fluorine-containing organic compound and catalyst. It is therefore possible to drop the silane compound of the formula (3) to the reaction vessel in which the fluorine-containing organosilicon compound of the formula (2) and the catalyst for addition-reaction have been charged. It is also -possible to charge the fluorine-containing organic compound, silane compound and catalyst in a reaction vessel in advance, and the reaction vessel may be heated to a given temperature to carry out the addition-reaction. Because the addition-reaction is exothermic, care should always be taken in the reaction temperature control.

It should also be noted that a polymerization inhibitor such as 2,6-di-tert-butyl-p-cresol should preferably be used during the addition-reaction to prevent excessive polymerization reaction.

Said silane compound and the fluorine-containing organic compound are used in such amounts that 0.8 to 2 mols, more preferably 1 to 1.5 mols, of the silane compound may be present per mol of the fluorine-containing organic compound. The catalyst is normally used in an amount ranging between $1\times10^{-6}$ to $1\times10^{-2}$ mol, more preferably between $1\times10^{-5}$ to $1\times10^{-3}$ mol.

A solvent may be optionally used in the addition-reaction, but the reaction normally proceeds smoothly without a solvent.

According to the present invention, a fluorine-containing organosilicon compound in which the hydrolizable group X is an alkoxy group represented by $-OR^3$ (wherein $R^3$ is as defined above) may be produced by reacting a fluorine-containing organosilicon compound of the invention wherein X is a halogen atom with an alcohol expressed by $R^3OH$ (wherein $R^3$ is as defined above) (so-called alkoxylation reaction). As this reaction generates hydrogen halide, it is preferable to use a scavenger such as tertiary amines, urea, metal alkoxides, orthoformates and epoxy compounds.

According to the present invention, a fluorine-containing organosilicon compound in which the hydrolizable group X is an amino group represented by $-NR^4R^5$ (wherein $R^4$ and $R^5$ are as defined above) may be obtained by reacting a fluorine-containing organosilicon compound of the present invention wherein X is a halogen atom with a secondary amine compound represented by $NHR^4R^5$ (wherein $R^4$ and $R^5$ are as defined above). This reaction also generates hydrogen halide, but in this case, the starting material $NHR^4R^5$ also acts as its scavenger.

Use

The fluorine-containing organosilicon compound of the present invention contains a hydrolizable group which is reactive with glass, metal or silica, and an acryloxyl group or methacryloxyl group which is reactive with an organic material such as synthetic resins, and further contains a fluorine-containing group. Thus, it can be used as a silane coupling agent for laminated sheets of polyester resin and glass to improve their mechanical strength and electric properties as well as water and heat resistances. By adding the compound of the present invention to polyester resin concrete, it not only improves the strength but water and heat resistances as well.

EXAMPLES

Example 1

Into a 100 ml stainless steel resisting pressure vessel are charged 19.0 g (0.069 mol) of a fluorine-containing organic compound having the formula:

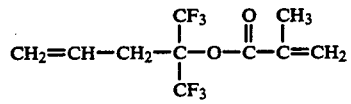

16.2 g (0.120 mol) of $Cl_3SiH$, 0.32 g (Pt: $3.2\times10^{-5}$ mol) of 2-ethylhexanol modified complex of $H_2PtCl_6$ (Pt concentration: 2 weight %) and 0.003 g of B.H.T (2,6-di-tert-butyl-p-cresol) as a polymerizaion inhibitor, and they were reacted by heating at 115° C. for 16 hours. The reaction mixture was distilled in vacuum to obtain 14.7 g of a product at 88°–90° C./4 mmHg (yield: 52%).

The compound thus obtained was subjected to $^1H$-NMR, infrared absorption spectroscopy, element analysis and mass spectrometry. The results are shown below.

The results given below indicate that the compound obtained is represented by the following formula:

$$Cl_3SiCH_2CH_2CH_2-\underset{\underset{CF_3}{|}}{\overset{\overset{CF_3}{|}}{C}}-O-\overset{\overset{O}{\|}}{C}-\underset{}{\overset{\overset{CH_3}{|}}{C}}=CH_2$$

(1) ¹H-NMR; solvent CCl₄, internal standard TMS 1.5 ppm (m, 4H, CH₂, —CH₂—CH₂, Si—CH₂); 1.9 ppm (S, 3H, —CH₃—); 2.5 ppm (m, 2H, —CH₂—C(CF₃)₂); 5.7 ppm (s, 1H, $$\underset{O}{\overset{}{\underset{\|}{C}}}\diagdown\overset{H_3C}{\diagup}C=C\diagdown\overset{H}{\diagup}_{H)}$$

6.0 ppm (s, 1H, $$\underset{O}{\overset{}{\underset{\|}{C}}}\diagdown\overset{H_3C}{\diagup}C=C\diagdown\overset{H}{\diagup}_{\underline{H})}$$

(2) Infrared absorption spectroscopy; KBr method 1760 (cm⁻¹) (C=O); 1260, 1220, 1140, 1030 (cm⁻¹); 590 (cm⁻¹) (Si—Cl).

(3) Element analysis: as $C_{10}H_{11}O_2Cl_3F_6Si$

|  | C(%) | H(%) | F(%) | Si(%) |
| --- | --- | --- | --- | --- |
| Calculated | 29.18 | 2.69 | 27.69 | 6.82 |
| Found | 29.45 | 2.80 | 27.11 | 6.05 |

(4) MS: 410 (M+).

EXAMPLE 2

Into a 50 ml flask equipped with a thermometer, a coiled condenser and a magnetic stirrer were charged 3.0 g (0.0941 mol) of methanol and 2.8 g (0.0466 mol) of urea. Droplets of the fluorine-containing organosilicon compound obtained in Example 1 and having the formula:

$$Cl_3SiCH_2CH_2CH_2-\underset{\underset{CF_3}{|}}{\overset{\overset{CF_3}{|}}{C}}-O-\overset{\overset{O}{\|}}{C}-\underset{}{\overset{\overset{CH_3}{|}}{C}}=CH_2$$

in an amount of 11.7 g (0.0285 mol) were gradually added to the mixture under nitrogen stream using a dropping funnel. The temperature inside the flask during dropping rose from 25° C. to 35° C. The reaction was continued for one hour under agitation, and a urea salt in a slurry form was separated. The residual mixture was distilled in vacuum to obtain 9.13 g of the reaction product at 100°-101° C./4 mmHg (yield: 80.4%).

The compound thus obtained was subjected to ¹H-NMR, infrared absorption spectroscopy, element analysis and mass spectrometry. The results are shown below.

The results indicate that the compound obtained is represented by the following formula:

$$(CH_3O)_3SiCH_2CH_2CH_2-\underset{\underset{CF_3}{|}}{\overset{\overset{CF_3}{|}}{C}}-O-\overset{\overset{O}{\|}}{C}-\underset{}{\overset{\overset{CH_3}{|}}{C}}=CH_2$$

(1) ¹H-NMR: solvent CCl₄, internal standard TMS 0.7 ppm (m, 2H, CH₂—Si); 1.4 ppm (m, 2H, CH₂—CH₂—CH₂); 1.9 ppm (s, 3H, C—CH₃); 2.5 ppm (m, 2H, $$-CH_2-\underset{\underset{CF_3)}{|}}{\overset{\overset{CF_3}{|}}{C}}-$$

3.4 ppm (s, 9H, —O—CH₃)
5.7 ppm (s, 1H, $$\underset{O}{\overset{}{\underset{\|}{C}}}\diagdown\overset{H_3C}{\diagup}C=C\diagdown\overset{H}{\diagup}_{H)}$$

6.0 ppm (s, 1H, $$\underset{O}{\overset{}{\underset{\|}{C}}}\diagdown\overset{H_3C}{\diagup}C=C\diagdown\overset{H}{\diagup}_{\underline{H})}$$

(2) Infrared absorption spectroscopy; KBr method 2950 (cm⁻¹); 2850 (cm⁻¹) [C—H(Si—OCH₃)]; 1760 (cm⁻¹) (C=O); 1320, 1260, 1220, 1030, 820 (cm⁻¹).

(3) Element analysis: as $C_{13}H_{20}O_5F_6Si$

|  | C(%) | H(%) | F(%) | Si(%) |
| --- | --- | --- | --- | --- |
| Calculated | 39.20 | 5.06 | 28.61 | 7.05 |
| Found | 39.96 | 5.57 | 28.09 | 7.51 |

(4) MS: 398 (M+).

What is claimed is:

1. A fluorine-containing organosilicon compound having the formula (1):

$$X_n(R^1)_{3-n}SiCH_2CH_2(CH_2)_m-\underset{\underset{CF_3}{|}}{\overset{\overset{CF_3}{|}}{C}}-O-\overset{\overset{O}{\|}}{C}-\underset{}{\overset{\overset{R^2}{|}}{C}}=CH_2 \quad (1)$$

wherein X is a hydrolyzable group, R¹ is a monovalent organic group, R² is a methyl group or a hydrogen atom, n is an integer of 1, 2 or 3, and m is an integer of 0 or 1.

2. A fluorine-containing organosilicon compound as claimed in claim 1 wherein, in the formula (1), X is a lower alkoxy group or a halogen atom, R¹ is a lower alkyl group, and R² is a methyl group or a hydrogen atom.

3. A process of producing a fluorine-containing organosilicon compound as claimed in claim 1, which comprises effecting addition-reaction of a fluorine-containing organic compound having the formula (2):

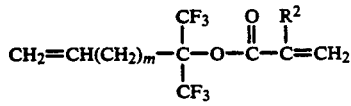 (2)

wherein R² is a methyl group or a hydrogen atom and m is an integer of 0 or 1, with a silane compound having the formula (3):

$$X_n(R^1)_{3-n}SiH \qquad (3)$$

wherein X is a hydrolyzable group, R¹ is a monovalent organic group, and n is an integer of 1, 2 or 3, in the presence of a transition metal or its compound.

4. A process of producing a fluorine-containing organosilicon compound having the formula (1) wherein X is an alkoxy group represented by —OR³ where R³ is a monovalent organic group, which comprises reacting a fluorine-containing organosilicon compound having the formula (1) wherein X is a halogen atom with an alcohol formula R³OH where R³ is as defined above.

5. A process of producing a fluorine-containing organosilicon compound having the formula (1) wherein X is an amino group represented by —NR⁴R⁵ where R⁴ and R⁵ may be the same or different and are each a monovalent organic group, which comprises reacting a fluorine-containing organosilicon compound having the formula (1) wherein X is a halogen atom with an amine compound having the formula NHR⁴R⁵ where R⁴ and R⁵ are as defined above.

* * * * *